(12) United States Patent
Uhrich et al.

(10) Patent No.: US 7,470,802 B2
(45) Date of Patent: Dec. 30, 2008

(54) MICELLE ASSEMBLIES

(75) Inventors: Kathryn E. Uhrich, Plainfield, NJ (US); Lu Tian, Morrisville, PA (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 98 days.

(21) Appl. No.: 11/006,506

(22) Filed: Dec. 7, 2004

(65) Prior Publication Data

US 2006/0039964 A1    Feb. 23, 2006

Related U.S. Application Data

(63) Continuation of application No. PCT/US03/17902, filed on Jun. 6, 2003.

(60) Provisional application No. 60/386,920, filed on Jun. 7, 2002.

(51) Int. Cl.
*C07C 53/00* (2006.01)
*C07C 57/00* (2006.01)

(52) U.S. Cl. ..................... 554/227; 424/450

(58) Field of Classification Search .............. 554/64
See application file for complete search history.

(56) References Cited

U.S. PATENT DOCUMENTS

| | | | | |
|---|---|---|---|---|
| 4,065,598 | A * | 12/1977 | Takahashi et al. | ........... 428/394 |
| 6,328,988 | B1 | 12/2001 | Uhrich | |
| 6,365,146 | B1 | 4/2002 | Uhrich | |
| 6,497,895 | B2 | 12/2002 | Uhrich | |
| 2004/0198641 | A1 | 10/2004 | Uhrich et al. | |
| 2005/0089504 | A1 | 4/2005 | Uhrich et al. | |

FOREIGN PATENT DOCUMENTS

| | | |
|---|---|---|
| WO | WO 00/65024 | 2/2000 |
| WO | WO 03/005959 | 1/2003 |

OTHER PUBLICATIONS

Chem. Abstr of JP-6305820, 1994.*
Liu et al., "Unimolecular micelles: Synthesis and characterization of amphiphillic polymer systems", *Journal of Polymer Science, Part A; Polymer Chemistry*, 37(6), 703-711 (1999).
Tian et al., "Design and synthesis of amphiphillic poly(ethylene glycol) derivatives as a micellar drug delivery system", *Polymer Preprints*, 43(2), 719-720 (2002).

(Continued)

*Primary Examiner*—Deborah D Carr
(74) *Attorney, Agent, or Firm*—Viksnins Harris & Padys PLLP

(57) ABSTRACT

The invention encompasses micelle assemblies, compositions having micelle assemblies, and methods for preparing micelle assemblies and compositions thereof. Also, the invention encompasses compounds of the formula: A-X-Y-Z-R$_1$ wherein A is a carboxy group or is absent; X is a polyol, Y is —C(=O)—, —C(=S)—, or is absent; Z is O, S, or NH; and R$_1$ is a polyether, wherein one or more hydroxy groups of the polyol are acylated with a fatty acid residue, wherein the compounds form micelle assemblies. The invention encompasses methods of encapsulating molecules using the compounds of the invention.

18 Claims, 8 Drawing Sheets

OTHER PUBLICATIONS

Tian et al., "Design and synthesis of amphiphilic poly(ethylene glycol) derivatives as a micellar drug delivery system", *Abstracts of Papers, Part 2*, 224, (1-2), abstract 748, 224th ACS National Meeting (2002).

International PCT Search Report for PCT/US 03/17902, (Jun. 06, 2003), 5 pgs.

Allen, C. et al. (1999) "Nano-engineering block copolymer aggregates for drug delivery." *Colloids and Surfaces B: Biointerfaces* 16:3-27.

Kataoka, K. et al. (2001) "Block copolymer micelles for drug delivery: design, characterization and biological significance." *Adv Drug Deliv Rev.* 47(1):113-31.

Moore, J.S., et al. (1990) "Room temperature polyesterification." *Macromolecules* 23(1):65-70.

Otsuka, H. et al. (2001) "Self-assembly of poly(ethylene glycol)-based block copolymers for biomedical applications." *Current Opinion in Colloid & Interface Science* 6(1):3-10.

Torchilin, V.P. (2001) "Structure and design of polymeric surfactant-based drug delivery systems." *J Control Release* 73(2-3):137-72.

\* cited by examiner

MICELLE ASSEMBLIES

CROSS-REFERENCE TO RELATED APPLICATIONS

This application is a continuation under 35 U.S.C. 111(a) of PCT/US03/17902, filed on Jun. 6, 2003 and published in English on Dec. 18, 2003 as WO 03/103594 A2, which claimed priority under 35 U.S.C. 119(e) of U.S. Provisional Application Ser. No. 60/386,920, filed Jun. 7, 2002, which applications and publication are incorporated herein by reference.

GOVERNMENT FUNDING

The invention described herein was made with government support under Grant Number (BES-9983272), awarded by the National Science Foundation. The United States Government has certain rights in the invention.

BACKGROUND OF THE INVENTION

Polymeric micelles are self-assembled amphiphilic block copolymers. These micelles have attracted attention as promising colloidal drug delivery systems (V. P. Torchilin *J. Controlled. Release.* 2001, 73, 137; C. Allen, D. et al., *Colloids and Surfaces B: Biointerfaces* 1999, 16, 3; and H. Otsuka, et al., *Current Opinion in Colloid & Interface Science* 2001, 6, 3). In these colloidal systems, the hydrophobic block typically forms the core, essentially a "microcontainer" for a lipophilic pharmaceutical (K. Kataoka, et al., *Adv. Drug Delivery Rev.* 2001, 47, 113). The hydrophilic part forms the outer shell, stabilizing the interface between the core and the external aqueous environment. Compared to traditional micellar systems, these polymeric surfactant-based drug carriers display apparent advantages such as lower critical micelle concentration (CMC), improved bioavailability, reduction of toxicity, enhanced permeability across the physiological barriers, and substantial changes in drug biodistribution.

Amphiphilic star-like macromolecules (ASMs) have also been studied for drug delivery applications. (See, e.g., U.S. patent application Ser. No. 09/298,729 filed Apr. 23, 1999; U.S. patent application Ser. No. 09/422,295, filed Oct. 21, 1999, and International Patent Application US00/10050 filed Apr. 18, 2000). The core-shell, amphiphilic structure of ASMs is covalently linked, which makes it thermodynamically stable compared to conventional micellar systems. Thus, ASM's offer numerous advantages over conventional micellar systems. Despite these advantages, the use of ASM's is somewhat limited due to the difficulty and cost associated with their preparation. Accordingly, there is a need for additional micellar systems and reverse micellar systems that possess some of the advantages associated with the thermodynamic stability of ASM's, but which are easier and less expensive to prepare.

SUMMARY OF THE INVENTION

Applicant has discovered that compounds of formula (I):

A-X-Y-Z-R$_1$    (I)

wherein A is a carboxy group or is absent; X is a polyol, Y is —C(=O)—, —C(=S)—, or is absent; Z is O, S or NH; and R$_1$ is a polyether, wherein one or more hydroxy groups of the polyol are acylated with a fatty acid residue, will aggregate in a solvent to form micellar structures (e.g., see FIG. 2).

Additionally, compounds of formula (I) having unsaturated bonds (e.g., in the fatty acid or polyether groups), can be cross-linked after aggregate formation to form covalently bound structures (i.e. cross-linked micelles). These aggregates, both cross-linked and uncross-linked, are useful in drug delivery applications, as well as in many other applications where traditional micelles and ASM's can be applied. The aggregates formed from compounds of formula (I), both cross-linked and uncross-linked, can be prepared without much of the difficulty and cost associated with the preparation of ASM's.

Accordingly, the invention provides a compound of formula (I) as described above. Such compounds of formula (I) are useful intermediates for preparing aggregates that can be used in drug delivery applications and that can be cross-linked to provide cross-linked micelles that are also useful in drug delivery applications.

The invention also provides a composition comprising a plurality of compounds of formula (I) in a solvent. Such a composition is useful for preparing aggregates and cross-linked micelles comprising compounds of formula (I).

The invention also provides a composition comprising a plurality of compounds of formula (I) in a solvent, wherein the compounds of formula (I) are associated into one or more aggregates.

The invention also provides a composition comprising a cross-linked micelle that is formed from plurality of compounds of formula (I) in a solvent, wherein the compounds of formula (I) form one or more aggregate structures and have been cross-linked to provide the cross-linked micelle.

The invention also provides an encapsulate comprising a molecule surrounded or partially surrounded by an aggregate or a cross-linked micelle of the invention.

The invention also provides a method for preparing a cross-linked micelle of the invention comprising cross-linking aggregates comprising a plurality of compounds of formula (I) to provide the cross-linked micelle. The invention further provides a method where the aggregates are formed by combining a plurality of compounds of formula (I) in a solvent.

The invention also provides a method for preparing an encapsulate of the invention comprising combining a plurality of compounds of formula (I) and a molecule (e.g., a therapeutic agent) in a solvent, and allowing the compounds of formula (I) to aggregate around the molecule, to provide the encapsulate (i.e. the molecule surrounded or partially surrounded by a plurality of compounds of formula (I)).

The invention also provides a method for preparing an encapsulate of the invention comprising combining a plurality of compounds of formula (I) and a molecule (e.g., a therapeutic agent) in a solvent, allowing the compounds of formula (I) to aggregate around the molecule, and cross-linking the compounds of formula (I) to provide the encapsulate (i.e. the molecule encapsulated in a cross-linked micelle).

The invention also provides a composition comprising a solvent, and an aggregate of a plurality of compounds of formula (I) surrounding a molecule (e.g., a therapeutic agent).

The invention also provides a pharmaceutical composition comprising an encapsulate of the invention (i.e. a therapeutic agent surrounded or partially surrounded by a plurality of compounds of formula (I)); and a pharmaceutically acceptable carrier.

The invention also provides a pharmaceutical composition comprising an encapsulate of the invention (i.e. a therapeutic agent encapsulated in a cross-linked micelle); and a pharmaceutically acceptable carrier.

The invention also provides a method for delivering a therapeutic agent to an animal in need of treatment with the agent comprising administering an encapsulate of the invention comprising the agent to the animal.

The invention also provides intermediates and processes useful for preparing compounds of formula (I) as described herein.

DETAILED DESCRIPTION

Figure 1:
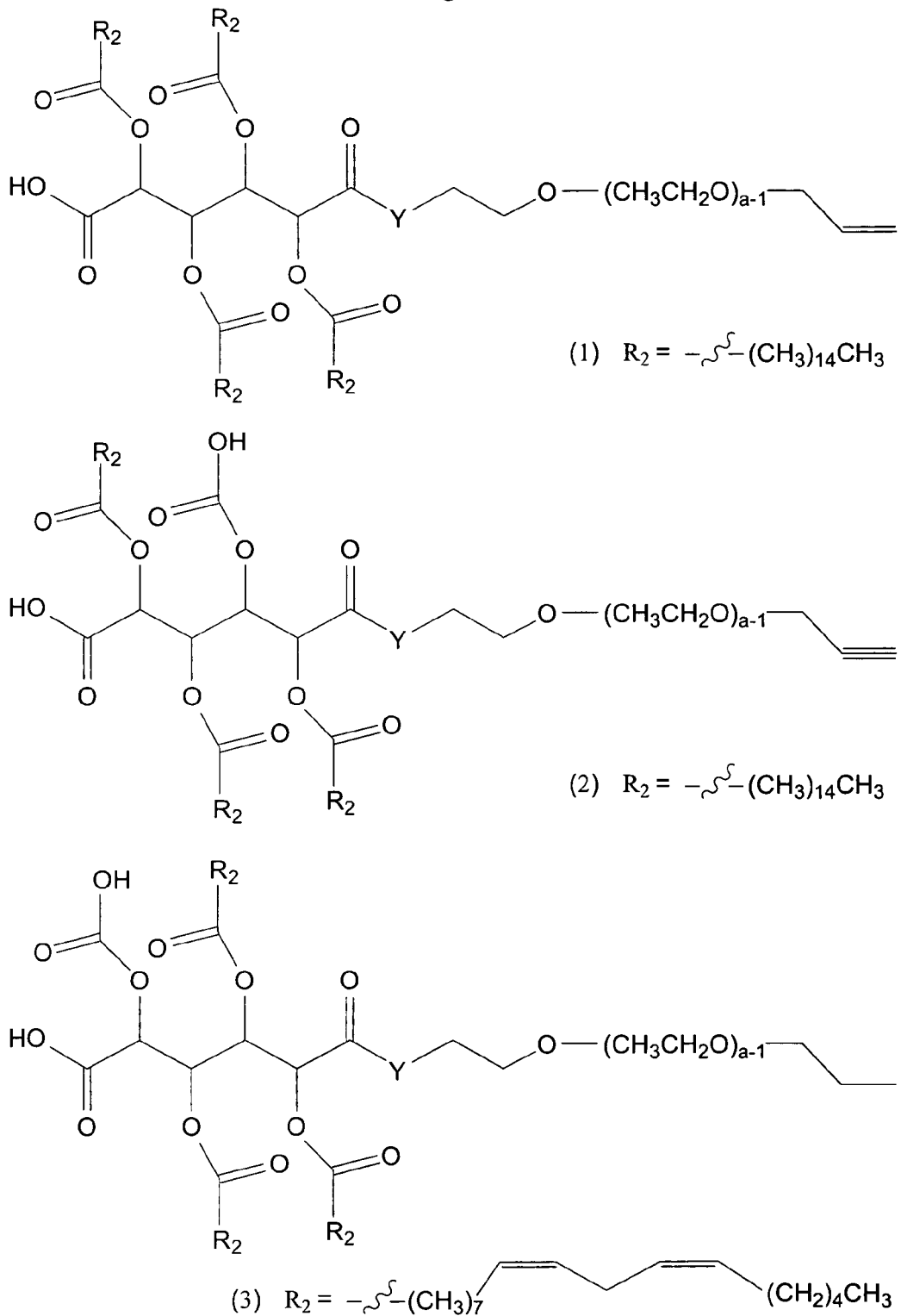
FIG. 1 shows representative compounds of formula (I) (1-3).
Figure 2:
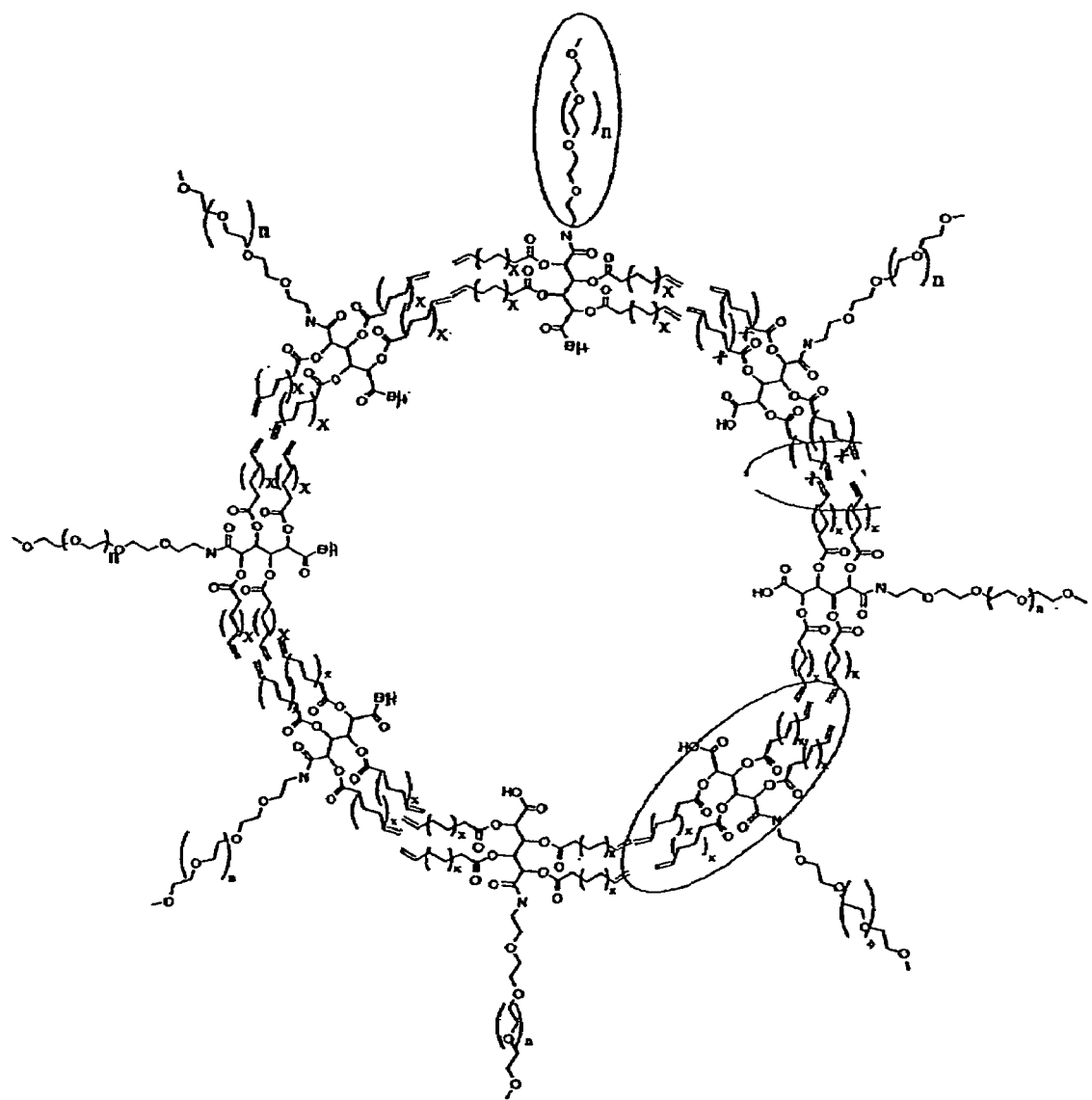
FIG. 2 shows an aggregate of a plurality of compounds of formula (I) prior to cross-linking.
Figure 3:
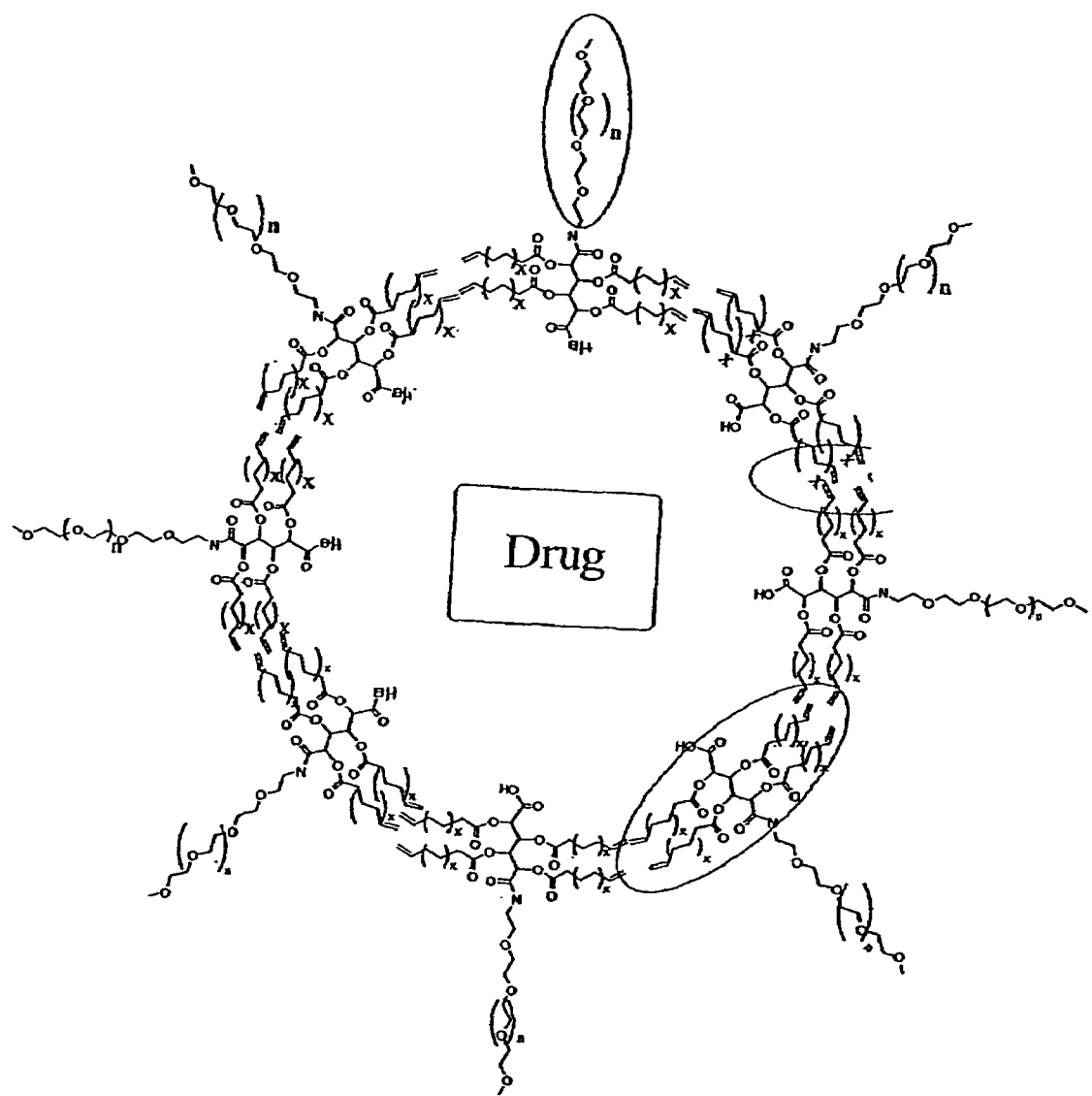
FIG. 3 shows an encapsulate of the invention prior to cross-linking, with a molecule (e.g. "Drug") encapsulated in an aggregate made up of a plurality of compounds of formula (I).
Figure 4:
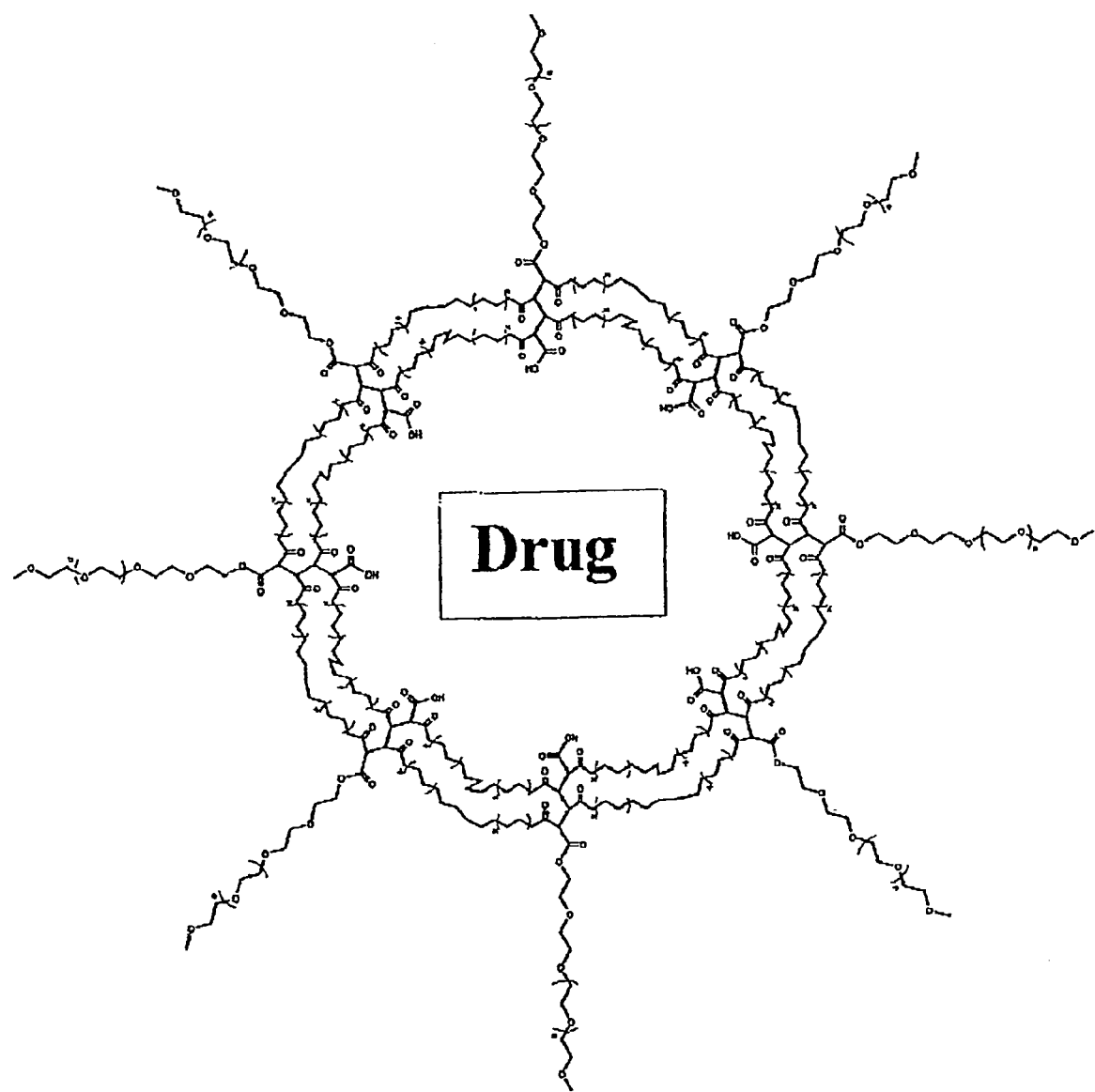
FIG. 4 shows the encapsulate of FIG. 3 after cross-linking to provide a molecule (e.g. "Drug") encapsulated in a cross-linked micelle.

A is a carboxy group or is absent. When present, A may optionally be substituted with or attached to a bioactive or therapeutically active molecule. The bioactive or therapeutically active molecule can be any known to one of ordinary skill in the art such as those described below. In a most preferred embodiment, the bioactive or therapeutically active molecule includes, but is not limited to, vitamin E, sulfonic acids, sulfonates, or salicylic acid.

As used herein the term "polyol" includes straight chain and branched chain aliphatic groups, as well as mono-cyclic and poly-cyclic aliphatics, which are substituted with two or more hydroxy groups. A polyol typically has from about 2 carbons to about 20 carbons; preferably, from about 3 carbons to about 12 carbons; and more preferably from about 4 carbons to about 10 carbons. A polyol also typically comprises from about 2 to about 20 hydroxy groups; preferably from about 2 to about 12 hydroxy groups; and more preferably from about 2 to about 10 hydroxy groups. A polyol can also optionally be substituted on a carbon atom with one or more (e.g., 1, 2, or 3) carboxy groups (COOH). These carboxy groups can conveniently be used to link the polyol to the polyether in a compound of formula (I).

One specific polyol is a mono- or di-carboxyilic acid containing from 1 to about 10 carbon atoms and substituted with from 1 to about 10 hydroxyl groups. The mono- or di-carboxylic acid may be a straight chained or branched chained aliphatic, or a mono-cyclic or poly-cyclic aliphatic compound. Suitable dicarboxylic acids include mucic acid, malic acid, citromalic acid, alkylmalic acid, hydroxy derivatives of glutaric acid, and alkyl glutaric acids, tartaric acid, citric acid, hydroxy derivatives of rumadic acid, and the like. Suitable monocarboxylic acids include 2,2-(bis(hydroxymethyl)propionic acid, and N-[tris(hydroxymethyl)methyl]glycine (tricine).

Another specific polyol is a "saccharide," which includes monosaccharides, disaccharides, trisaccharides, polysaccharides and sugar alcohols. The term includes glucose, sucrose, fructose and ribose, as well as deoxy sugars such as deoxyribose and the like. Saccharide derivatives can conveniently be prepared by methods known to the art. Examples of suitable mono-saccharides are xylose, arabinose, and ribose. Examples of di-saccharides are maltose, lactose, and sucrose. Examples of suitable sugar-alcohols are erythritol and sorbitol.

As used herein, the term polyether includes poly(alkylene oxides) having between about 2 and about 150 repeating units. Typically, the poly(alkylene oxides) have between about 50 and about 110 repeating units. The alkylene oxide units contain from 2 to 10 carbon atoms and may be straight chained or branched. Preferably, the alkylene oxide units contain from 2 to 10 carbon atoms. Poly(ethylene glycol) (PEG) is preferred. Alkoxy-, amino-, carboxy-, and sulfo-terminated poly(alkylene oxides) are preferred, with methoxy-terminated poly(alkylene oxides) being more preferred.

A preferred polyether has the following structure:

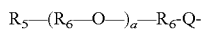

wherein $R_5$ is a 1 to 20 carbon straight-chain or branched alkyl group, —OH, —OR$_7$, —NH$_2$, —NHR$_7$, —NHR$_7$R$_8$, —CO$_2$H, —SO$_3$H (sulfo), —CH$_2$—OH, —CH$_2$—OR$_7$, —CH$_2$—O—CH$_2$—R$_7$, —CH$_2$—NH$_2$, —CH$_2$—NHR$_7$, —CH$_2$—NR$_7$R$_8$, —CH$_2$CO$_2$H, —CH$_2$SO$_3$H, or —O—C(=O)—CH$_2$—CH$_2$—C(=O)—O—;

$R_6$ is a 1 to 10 carbon straight-chain or branched divalent alkylene group;

each $R_7$ and $R_8$ is independently a 1 to 6 carbon straight-chain or branched alkylene group;

Q is —O—, —S—, or —NR$_7$; and a is an integer from 2 to 150, inclusive.

Another preferred polyether is methoxy terminated polyethylene glycol.

In a compound of formula (I), a poly(alkylene oxide) can be linked to the polyol, for example, through an ether, thioether, amine, ester, thioester, thioamide, or amide linkage. Preferably, a poly(alkylene oxide) is linked to the polyol by an ester or amide linkage in a compound of formula (I).

As used herein, the term fatty acid includes fatty acids and fatty oils as conventionally defined, for example, long-chain aliphatic acids that are found in natural fats and oils. Fatty acids typically comprise from about 2 to about 24 carbon atoms. Preferably, fatty acids comprise from about 6 to about 18 carbon atoms. The term "fatty acid" encompasses compounds possessing a straight or branched aliphatic chain and an acid group, such as a carboxylate, sulfonate, phosphate, phosphonate, and the like. The "fatty acid" compounds are capable of "esterifying" or forming a similar chemical linkage with hydroxy groups on the polyol. Examples of suitable fatty acids include caprylic, capric, lauric, myristic, myristoleic, palmitic, palmitoleic, stearic, oleic, linoleic, eleostearic, arachidic, behenic, erucic, and like acids. Fatty acids can be derived from suitable naturally occurring or synthetic fatty acids or oils, can be saturated or unsaturated, and can optionally include positional or geometric isomers. Many fatty acids or oils are commercially available or can be readily prepared or isolated using procedures known to those skilled in the art.

As used herein, the term "aggregate" means a plurality of compounds of formula (I) in a solvent that have organized into an ordered structure, for example, a structure having a hydrophobic core and a surrounding hydrophilic layer, or a structure having a hydrophilic core and a surrounding hydrophobic layer.

As used herein, the term "a plurality of compounds of formula (I)" means more than one compound of formula (I). In such a plurality, each compound of formula (I) can have the same structure, or the plurality can include compounds of formula (I) that have differing structures. In a preferred embodiment, the term "a plurality of compounds of formula (I)" means more than one compound of formula (I), wherein each of the compounds of formula (I) has the same structure.

As used herein, a "cross-linked micelle" means an aggregate that has been cross-linked to provide a covalently cross-linked structure.

As used herein, the term "encapsulate" means an aggregate, having a molecule (e.g., a therapeutic agent) surrounded or partially surrounded by a plurality of compounds of formula (I). The term encapsulate includes structures wherein the compounds of formula (I) have been cross-linked, as well as structures wherein the compounds of formula (I) have not been cross-linked.

As used herein, the term "stabilized encapsulate" means an aggregate, having a molecule (e.g., a therapeutic agent) surrounded or partially surrounded by a plurality of compounds of formula (I), wherein unsaturated bonds in the compounds of formula (I) have been cross-linked to provide a covalently stabilized structure.

Figure 5:
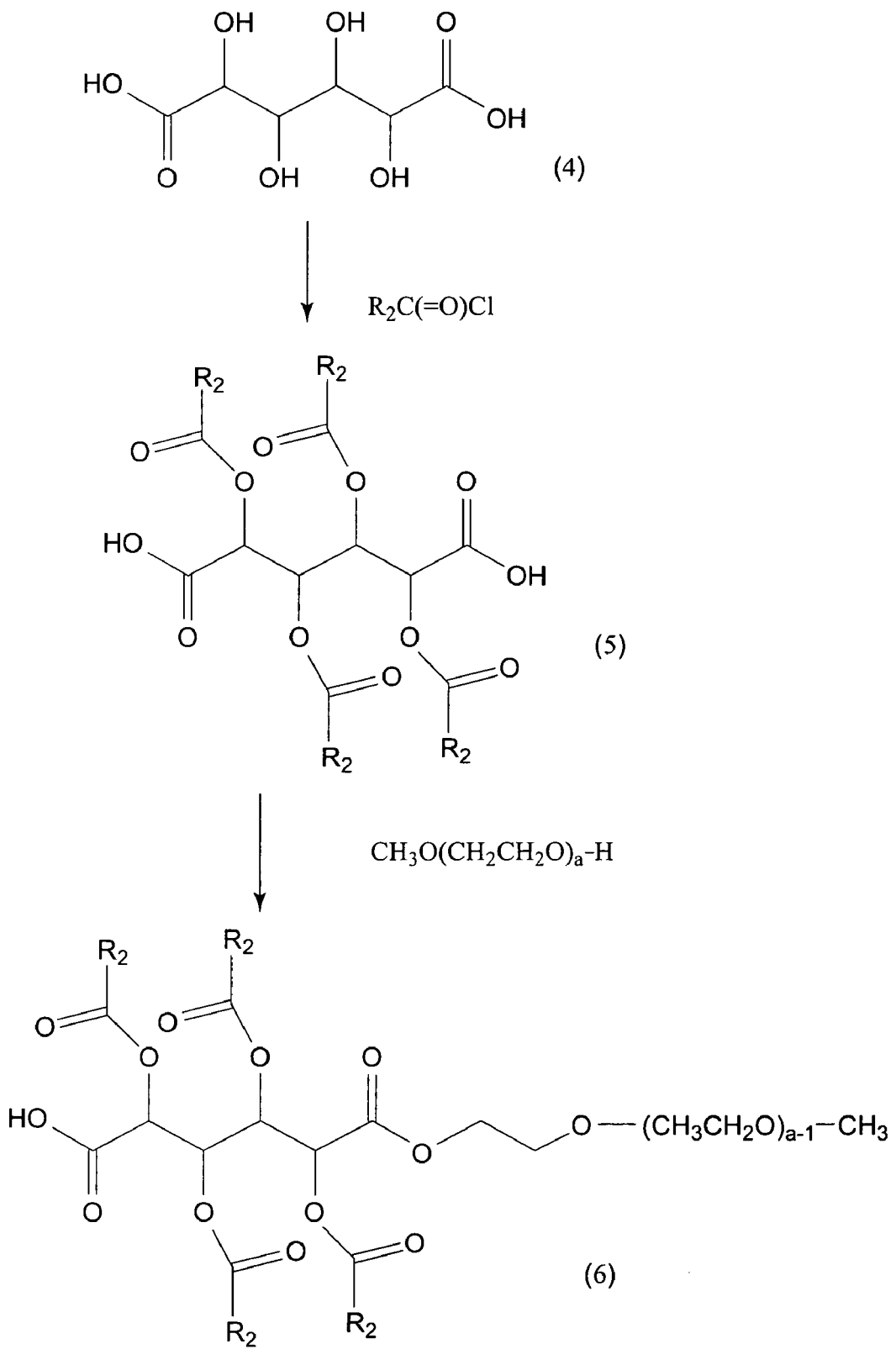
FIG. 5 Illustrates the syntheses of representative compounds of formula (I) (6).
Figure 6:
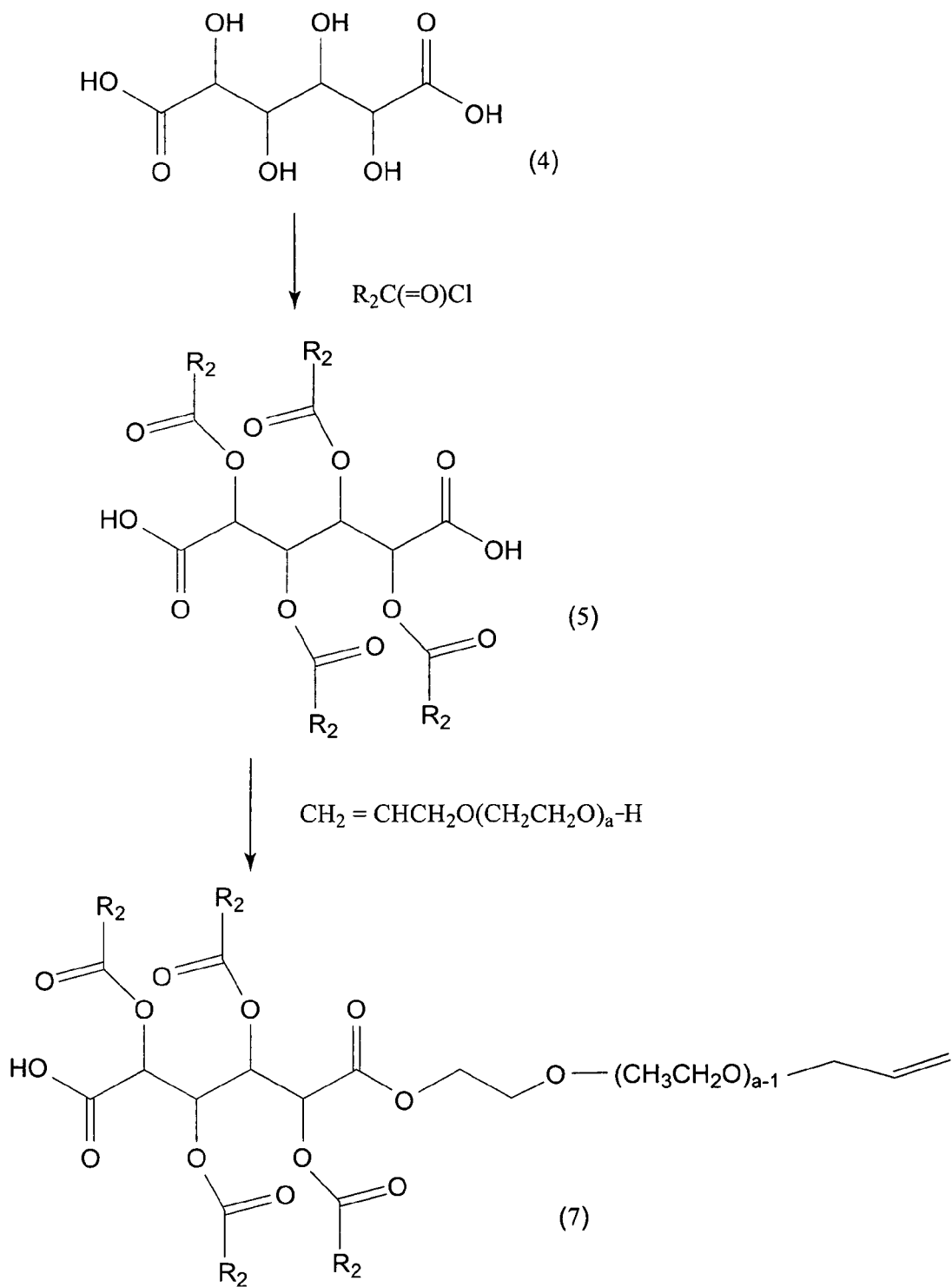
FIG. 6 Illustrates the syntheses of representative compounds of formula (I) (7).

As illustrated in FIG. 5, a representative compound of formula (I) can be prepared by acylating a polyol (4) by reaction with a stoichiometric excess of a fatty acid chloride to provide acylated polyol (5). Suitable conditions for such an acylation reaction are well known. For example, the reaction can be carried out in the presence of a catalyst, such as $ZnCl_2$, with heating. Suitable acylation conditions are illustrated in the Examples below. Coupling of (5) with a polyether, for example through an ester linkage, using a suitable coupling agent provides the compound of formula (I) (6).

When a plurality of compounds of formula (I) are placed in a hydrophilic solvent (e.g., an aqueous solution comprising water), Applicant has discovered that the compounds of formula (I) will aggregate, with the polyether portion of the compounds extending into the hydrophilic solvent, and the fatty acid portions of the compounds forming a hydrophobic core. Such aggregates can solubilize a hydrophobic molecule (e.g., a hydrophobic therapeutic agent) in the aqueous solvent, by encapsulating the hydrophobic molecule in the fatty acid core of the aggregates. The hydrophobic molecule can typically be added to the solution of the compounds of formula (I) subsequent to aggregation, or the hydrophobic molecule can be added to the solution of the compounds of formula (I) prior to aggregation, allowing the aggregates to form around the molecule. Thus, the aggregates formed from the compounds of formula (I) can function similar to traditional micelles.

Aggregates formed from a plurality of compounds of formula (I) can also function like reverse micelles. When a plurality of compounds of formula (I) are placed in a hydrophobic solvent (e.g., an organic solvent like hexanes or methylene chloride), the compounds of formula (I) will aggregate, with the fatty acid portion of the compounds extending into the hydrophobic solvent, and the polyether portion of the compounds forming a hydrophilic core. Such aggregates can solubilize a hydrophilic molecule (e.g., a hydrophilic therapeutic agent) in the organic solvent, by encapsulating the hydrophilic molecule in the polyether core of the aggregates. The hydrophilic molecule can typically be added to the solution of the compounds of formula (I) subsequent to aggregation, or the hydrophilic molecule can be added to the solution of the compounds of formula (I) prior to aggregation, allowing the aggregates to form around the molecule.

Subsequent to aggregate formation, the compounds of formula (I) that comprise unsaturated bonds can be cross-linked to form cross-linked micelles, which comprise an aggregate of a plurality of compounds of formula (I) that have been covalently linked. These cross-linked micelles can also be used as solubilizing agents for a wide range of applications. In some cases, a molecule to be solubilized can be added to a solution comprising such cross-linked micelles, and the molecule can locate in the core of the cross-linked micelle, and thus, be solubilized.

Figure 8:
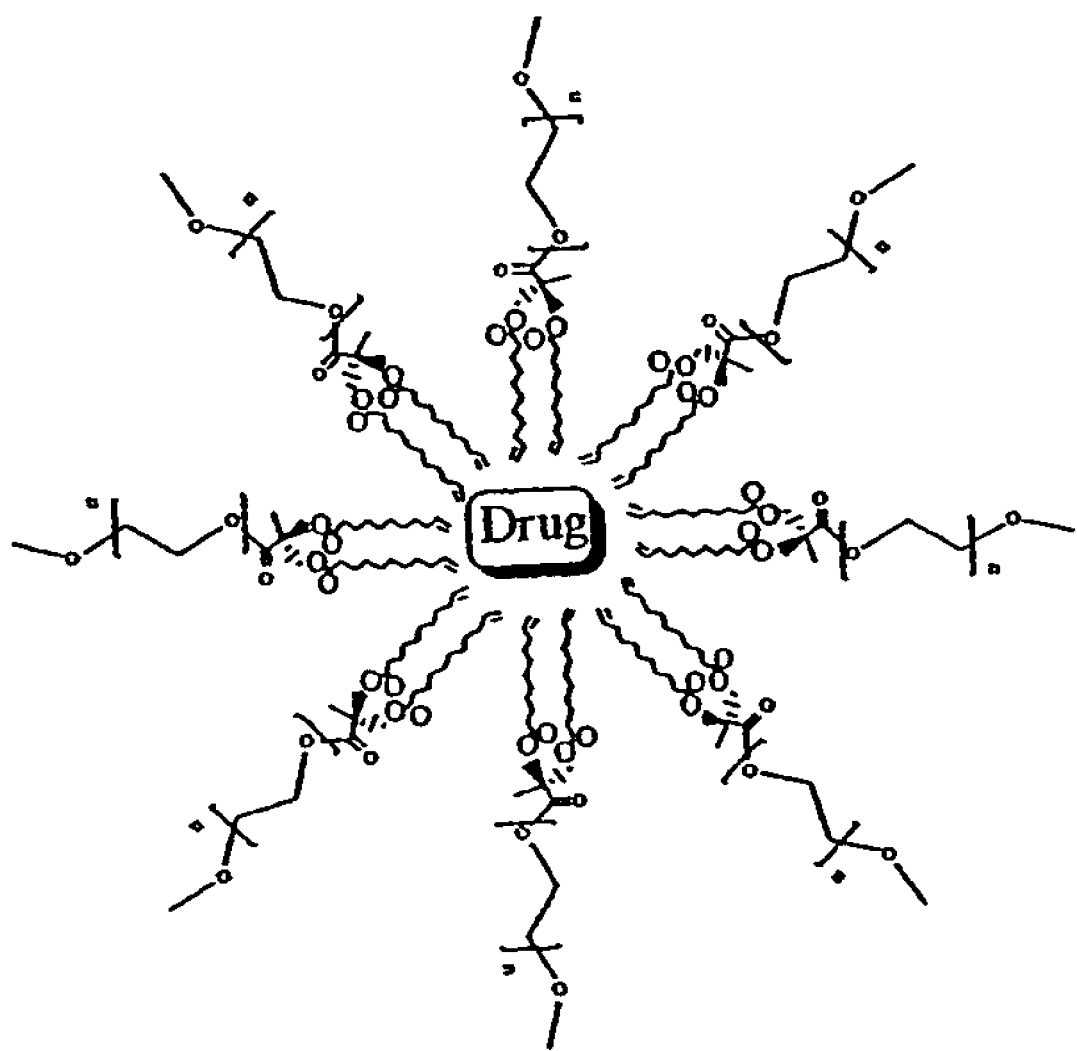
FIG. 8 shows an encapsulate of the invention, with a hydrophobic molecule (e.g. "Drug") encapsulated in an aggregate made up of a plurality of compounds of formula (I).

Covalently stabilized structures can also be formed by cross-linking unsaturated bonds in an encapsulate that comprises a molecule to be solubilized. For example, a hydrophobic molecule can be combined with a plurality of compounds of formula (I) in an aqueous solvent such that the compounds of formula (I) form aggregates around the hydrophobic molecule (See FIG. 8). After formation of the aggregates, the compounds of formula (I) can be cross-linked to provide a stabilized encapsulate.

Typically, the aggregates of the invention have a diameter of from about 10 nm to about 1000 nm. The diameters can be measured using any suitable analytical technique, such as, for example, dynamic light scattering.

Typically, cross-linked micelles of the invention have a number average molecular weight between about 1,000 and about 100,000 daltons, which can be measured using any suitable analytical technique, such as, for example, by Gel Permeation Chromatography relative to polystyrene standards.

Compounds of formula (I) can be used to form aggregates and cross-linked micelles that function similar to conventional "micelles" or "reverse micelles." These aggregates and cross-linked micelles can be used for essentially any application in which conventional micelles or reverse micelles are employed. Examples include drug solubilization, fragrance encapsulation, passive targeting for drug delivery, waste water treatment, enhanced capillary electrophoresis activation, and induction of protein crystallization.

Accordingly, as used herein, the term "molecule" includes any compound that can be incorporated into an aggregate or a cross-linked micelle as described herein. Typically, "molecules" have solubility properties that are undesirable and that can be modified by incorporation into an aggregate or a cross-linked micelle of the invention. For example, the term "molecule" includes therapeutic agents, insecticides, pesticides, herbicides, antiseptics, food additives, fragrances, dyes, diagnostic aids, and the like. Other specific examples of molecules include, but are not limited to:

abietic acid, aceglatone, acenaphthene, acenocoumarol, acetohexamide, acetomeroctol, acetoxolone, acetyldigitoxins, acetylene dibromide, acetylene dichloride, acetylsalicylic acid, alantolactone, aldrin, alexitol sodium, allethrin, allylestrenol, allyl sulfide, alprazolam, aluminum bis(acetylsalicylate), ambucetamide, aminochlothenoxazin, aminoglutethimide, amyl chloride, androstenediol, anethole trithone, anilazine, anthralin, Antimycin A, aplasmomycin, arsenoacetic acid, asiaticoside, astemizole, aurodox, aurothioglycamide, 8-azaguanine, azobenzene;

baicalein, Balsam Peru, Balsam Tolu, barban, baxtrobin, bendazac, bendazol, bendroflumethiazide, benomyl, benzathine, benzestrol, benzodepa, benzoxiquinone, benzphetamine, benzthiazide, benzyl benzoate, benzyl cinnamate, bibrocathol, bifenox, binapacryl, bioresmethrin, bisabolol, bisacodyl, bis(chlorophenoxy)methane, bismuth iodosubgallate, bismuth subgallate, bismuth tannate, Bisphenol A, bithionol, bomyl, bromoisovalerate, bomyl chloride, bomyl isovalerate, bomyl salicylate, brodifacoum, bromethalin, broxyquinoline, bufexamac, butamirate, butethal, buthiobate, butlated hydroxyanisole, butylated hydroxytoluene;

calcium iodostearate, calcium saccharate, calcium stearate, capobenic acid, captan, carbamazepine, carbocloral, carbophenothin, carboquone, carotene, carvacrol, cephaeline, cephalin, chaulmoogfic acid, chenodiol, chitin, chlordane, chlorfenac, chlorfenethol, chlorothalonil, chlorotrianisene, chlorprothixene, chlorquinaldol, chromonar, cilostazol, cinchonidine, citral, clinofibrate, clofazimine, clofibrate, cloflucarban, cionitrate, clopidol, clorindione, cloxazolam, coroxon, corticosterone, coumachlor, coumaphos, coumithoate cresyl acetate, crimidine, crifomate, cuprobam, cyamemazine, cyclandelate, cyclarbamate cymarin, cypennethril;

dapsone, defosfamide, deltamethrin, deoxycorticocosterone acetate, desoximetasone, 10 dextromoramide, diacetazoto, dialifor, diathymosulfone, decapthon, dichlofluani, dichlorophen, dichlorphenamide, dicofol, dicryl, dicmarol, dienestrol, diethylstilbestrol, difenamizole, dihydrocodeinone enol acetate, dihydroergotamine, dihydromorphine, dihydrotachysterol, dimestrol, dimethisterone, dioxathion, diphenane, N-(1,2-diphenylethyl)nicofinamide, dipyrocetyl, disulfamide, dithianone, doxenitoin, drazoxolon, durapatite, edifenphos, emodin, enfenamic acid, erbon, ergocominine, erythrityl tetranitrate, erythromycin stearate, estriol, ethaverine, ethisterone, ethyl biscomacetate, ethylhydrocupreine, ethyl menthane carboxamide, eugenol, euprocin, exalamide;

febarbamate, fenalamide, fenbendazole, fenipentol, fenitrothion, fenofibrate, fenquizone, fenthion, feprazone, flilpin, filixic acid, floctafenine, fluanisone, flumequine, fluocortin butyl, fluoxymesterone, flurothyl, flutazolam, fumagillin, 5-furfuryl-5-isopropylbarbutific acid, fusafungine, glafenine, glucagon, glutethimide, glybuthiazole, griseofulvin, guaiacol carbonate, guaiacol phosphate, halcinonide, hematoprphyrin, hexachlorophene, hexestrol, hexetidine, hexobarbital, hydrochlorothiazide, hydrocodone, ibuproxam, idebenone, indomethacin, inositol niacinate, iobenzamic acid, iocetamic acid, iodipamide, iomeglamic acid, ipodate, isomepheptene, isonoxin, 2-isovalerylindane-1,3-dione;

josamycin, 11-ketoprogesterone, laurocapram, 3-O-lauroylpyridoxol diacetate, lidocaine, lindane, linolenic acid, liothyronine, lucensomycin, mancozeb, mandelic acid, isoamyl ester, mazindol, mebendazole, mebhydroline, mebiquine, melarsoprol, melphalan, menadione, menthyl valerate, mephenoxalone, mephentermine, mephenyloin, meprylcaine, mestanolone, mestranol, mesulfen, metergoline, methallatal, methandriol, methaqualone, 3-methylcholanthrene, methylphenidate, 17-methyltestosterone, metipranolol, minaprine, myoral, nafialofos, nafiopidil, naphthalene, 2-naphthyl lactate, 2-(2-naphthyloxy)ethan01, naphthyl salicylate, naproxen, nealbarbital, nemadectin, niclosamide, nicoclonate, nicomorphine, nifuroquine, nifuroxazide, nitracrine, nitromersol, nogalamycin, nordazepam, norethandrolone, norgestrienone;

octavefine, oleandrin, oleic acid, oxazepam, oxazolam, oxeladin, oxwthazaine, oxycodone, oxymesterone, oxyphenistan acetate, paraherquamide, parathion, pemoline, pentaerythritol tetranitrate, pentylphenol, perphenazine, phencarbamide, pheniramine, 2-phenyl-6-chlorophenol, phentlmethylbarbituric acid, phenyloin, phosalone, phthalylsulfathiazole, phylloquinone, picadex, pifamine, piketopfen, piprozolin, pirozadil, plafibride, plaunotol, polaprezinc, polythiazide, probenecid, progesterone, promegestone, propanidid, propargite, propham, proquazone, protionamide, pyrimethamine, pyrimithate, pyrvinium pamoate;

quercetin, quinbolone, quizalofo-ethyl, rafoxamide, rescinnamine, rociverine, ronnel salen, scarlet red, siccmn, simazine, simetfide, sobuzoxane, solan, spironolactone, squalene, stanolone, sucralfate, sulfabenz, sulfaguanole, sulfasalazine, sulfoxide, sulpiride, suxibuzone, talbutal, terguide, testosterone, tetrabromocresol, tetrandrine, thiacetazone, thiocolchicine, thiocftc acid, thioquinox, thioridazine, thiram, thymyl N-isoamylcarbamate, tioxidazole, tioxolone, tocopherol, tolciclate, tolnafiate, triclosan, triflusal, tripara-nol;

ursolic acid, valinomycin, verapamil, vinblastine, vitamin A, vitamin D, vitamin E, xenbucin, xylazine, zaltoprofen, and zearalenone.

The aggregates and cross-linked micelles the invention are particularly useful for solubilizing hydrophobic molecules, particularly therapeutic agents that are hydrophobic in nature. Thus, according to one embodiment of the present invention, a therapeutic agent is encapsulated by combining the agent and a plurality of compounds of formula (I) in a solvent, such as water. After aggregates have formed (which can be determined, for example, by using dynamic light scattering, fluorescence spectroscopy, surface tension, or a combination thereof) the compounds of formula (I) are cross-linked to provide an encapsulate of the invention wherein the therapeutic agent is encapsulated in a cross-linked micelle.

The present invention contemplates the use of encapsulated hydrophobic molecules at concentrations as high as 1 M and greater, up to $10^6$ M. At the same time, another advantage of the present invention is the thermodynamic stability of the polymers, which permit the formation of low concentration stable aqueous solutions of the polymer encapsulates, far below the CMC's of conventional surfactants. Stable aqueous solutions with concentrations of $10^{-8}$ and greater are expected to have the greatest commercial utility. According to the invention, encapsulates are believed to form at concentrations below the presently available limits of detection, i.e., below $10^{-10}$ M.

The encapsulates of the invention that comprise a therapeutic agent can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the encapsulates of the invention may be systemically administered, e.g., orally, in combination with a pharmaceutically acceptable vehicle such as an inert diluent. They may be incorporated directly with the food of the patient's diet. For oral therapeutic administration, the encapsulates of the invention may be used in the form of elixirs, syrups, and the like.

The compositions may also contain a sweetening agent such as sucrose, fructose, lactose or aspartame or a flavoring agent such as peppermint, oil of wintergreen, or cherry flavoring may be added. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the encapsulates of the invention may be incorporated into sustained-release preparations and devices.

The encapsulates of the invention may also be administered intravenously or intraperitoneally by infusion or injection. Solutions of the encapsulates can be prepared, for example, in water. Under ordinary conditions of storage and use, these preparations may contain a preservative to prevent the growth of microorganisms.

The pharmaceutical dosage forms suitable for injection or infusion should be sterile, fluid and stable under the conditions of manufacture and storage. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions are prepared by incorporating the encapsulates of the invention in the required amount in the appropriate solvent with various of the other ingredients enumerated above, as required, followed by sterilization.

Encapsulation of molecules according to the invention modifies transdermal delivery of the molecule. Absorption through the skin can be increased or decreased by a factor of up to about 1000. Thus, the pharmaceutical dosage forms of present invention include dosage forms suitable for transdermal delivery, which, in addition to aqueous solutions, also include aqueous gels. The dosage form may be applied directly to the skin as a lotion, cream or salve, or a transdermal drug delivery device such as a transdermal patch may be employed, in which the encapsulated molecule is retained in the active agent reservoir of the patch.

The dose and method of administration will vary from animal to animal and be dependent upon such factors as the type of animal being treated, its sex, weight, diet, concurrent medication, overall clinical condition, the particular therapeutic agent employed, the specific use for which the agent is employed, and other factors which those skilled in the relevant field will recognize.

Therapeutically effective dosages may be determined by either in vitro or in vivo methods. For each particular dosage form of the present invention, individual determinations may be made to determine the optimal dosage required. The range of therapeutically effective dosages will naturally be influenced by the route of administration, the therapeutic objectives, and the condition of the patient. The determination of effective dosage levels, that is, the dosage levels necessary to achieve the desired result, will be within the ambit of one skilled in the art. Typically, applications of agent are commenced at lower dosage levels, with dosage levels being increased until the desired effect is achieved.

A typical dosage might range from about 0.001 mg to about 1,000 mg of therapeutic agent, per kg of animal weight. Preferred dosages range from about 0.01 mg/kg to about 100 mg/kg, and more preferably from about 0.10 mg/kg to about 20 mg/kg. Advantageously, the dosage forms of this invention may administered several times daily, and other dosage regimens may also be useful.

According to the invention, aggregate or cross-linked micelle degradation is not a prerequisite for release of the molecule (e.g. the therapeutic agent).

The compounds of Formula (I), aggregates, encapsulates and cross-linked micelles of the invention may also be used as thickening agents, lubricants, detergents surfactants, plasticizers and anti-fouling agents. The compounds of Formula (I), aggregates, encapsulates and cross-linked micelles of the invention may be used as an emulsifying, dispersing or stabilizing agent for dyes, cosmetics, pigment and pharmaceutical products. The compounds of Formula (I), aggregates encapsulates and cross-linked micelles of the invention are particularly useful as an, emulsifying, dispersing or stabilizing agent in the dyeing of textiles and for encapsulating dyes, fragrances, or both for cosmetics. The compounds of Formula (I), aggregates, encapsulates and cross-linked micelles of the invention are useful as lubricants and as a thickening agents for paints. The compounds of Formula (I), aggregates, encapsulates and cross-linked micelles of the invention may also be employed as an emulsifying, dispersing or stabilizing agent for components of photographic compositions and developers.

For therapeutic applications, the preferred cross-linked micelles and aggregates of the invention hydrolyze into components known to be biocompatible, i.e., sugars, fatty acids, amino acids and poly(ethylene glycol). This also results in low cytotoxicity of the polymer and its hydrolysis products.

The following non-limiting examples set forth hereinbelow illustrate certain aspects of the invention. All parts and percentages are by weight unless otherwise noted and all temperatures are in degrees Celsius.

All PEG's were obtained from Shearwater Polymers (Birmingham, Ala.) and used without further purification. All other chemicals were obtained from Aldrich (Milwaukee, Wis.), and used without further purification. Analytical grade solvents were used for all the reactions. Methylene chloride, tetrahydrofuran (THF), triethylamine (TEA) and dimethylsulfoxide (DMSO) were distilled. 4-(dimethylamino) pyridinium p-toluenesulfonate (DPTS) was prepared as described by J. S. Moore, S. I. Stupp *Macromolecules* 1990, 23, 65. $^1$H-NMR and spectra were recorded on a Varian 200 MHz or 400 MHz spectrometer. Samples (~5-10 mg/ml) were dissolved in $CDCl_3$ or $THF-d_4$, with the solvent used as an internal reference. IR spectra were recorded on a Mattson Series spectrophotometer by solvent casting samples onto a KBr pellet. Thermal analysis data were determined on a Perkin-Elmer Pyris 1 DSC system, samples (~10 mg) were heated under dry nitrogen gas. Data were collected at heating and cooling rates of 5° C./min. Gel permeation chromatography (GPC) was performed on a Perkin-Elmer Series 200 LC system. Dynamic laser scattering (DSL) measurements were carried on NICOMP particle sizing systems.

EXAMPLES

Example 1

Figure 7:
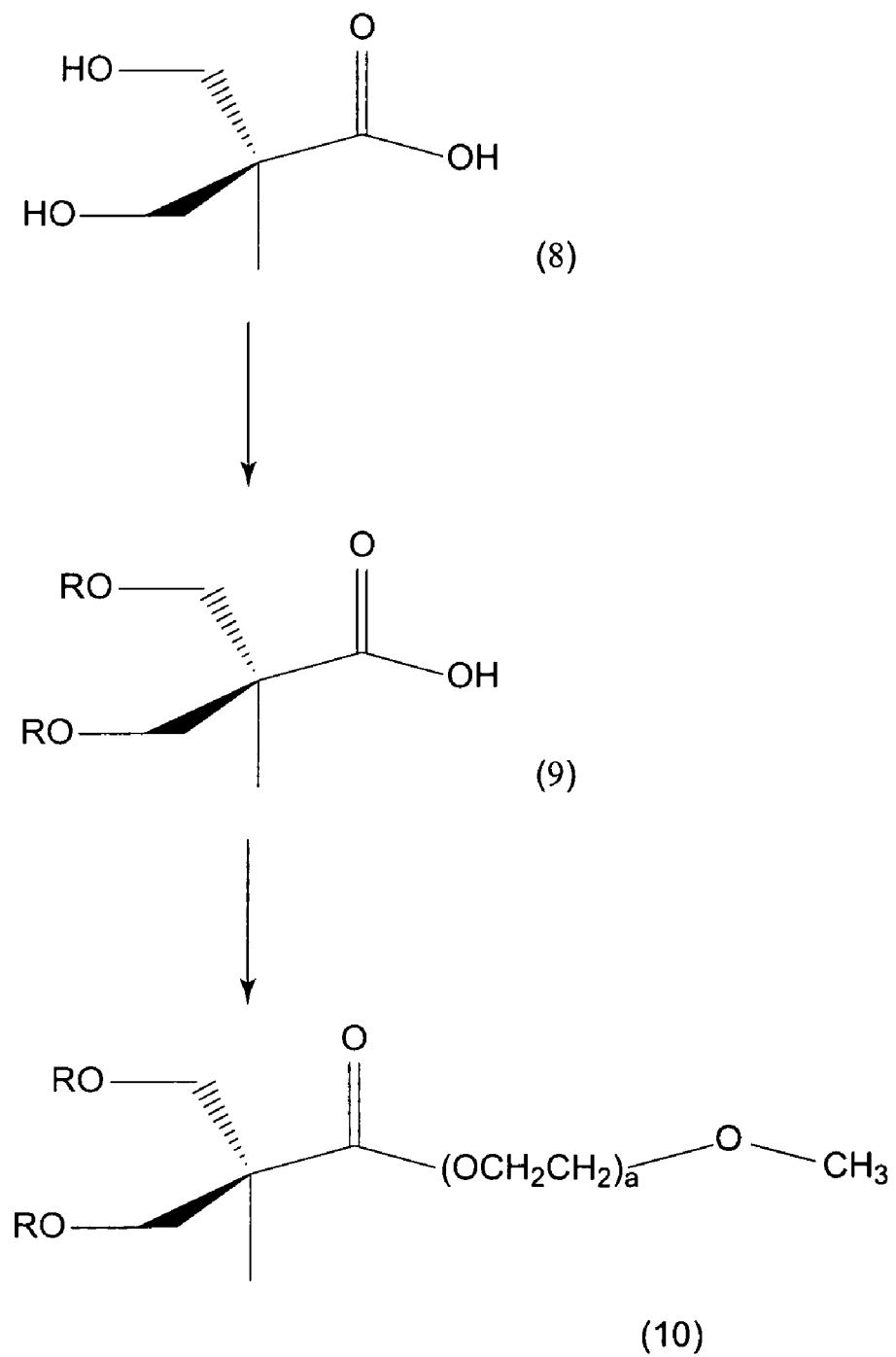
FIG. 7 Illustrates the syntheses of representative compounds of formula (I) (10).

Compound (10) (FIG. 7, R=10-undecenoyl)

mPEG5k (5.0 g, 1.0 mmol) was dehydrated by azeotropic distillation in toluene (30 ml), and the toluene was removed under vacuum. Compound (9) (1.4 g, 3.0 mmol) and DPTS (0.32 g, 1.0 mmol) in methylene chloride (30 ml) were added at room temperature. After 10 minutes flushing with nitrogen, 1.0 M DCC in methylene chloride (3.0 ml) was added dropwise. After 3 days, the DCC side product (dicyclohexylurea) was removed by suction filtration. The filtrate was washed with 30 ml portions of brine (3), dried over anhydrous sodium sulfate and evaporated to dryness The crude product was purified by precipitation into diethyl ether from methanol. The title compound was obtained as a white waxy solid (5.3 g), yield: 95%.

The intermediate Compound (9) was prepared as follows.

a. Compound (8). bis(Hydroxymethyl)propionic acid (DMPA, 2.0 g, 15 mmol) was dissolved into pyridine (25 ml). After 10 minutes flushing with nitrogen in ice/water bath, 10-undecenoyl chloride (7.4 ml, 34 mmol) was added dropwise. After 10 hours, the reaction mixture was poured into 0.1 N HCl solutions (300 ml) and stirred for 10 minutes. Ethyl ether (100 ml) was used to extract the product. The extraction was washed with 50 ml portions of brine (5), dried over anhydrous sodium sulfate, and evaporated to dryness. The crude product was purified by chromatography using petroleum ether:ethyl acetate (80:20) as eluent. Compound (9) was obtained as a colorless oil (5.0 g), yield: 72%.

Examples 2-4 detail the preparation of other acylated polyols that can be coupled with a polyether to provide compounds of formula (I).

Example 2

FIG. 5, Compound (5), $R_2$=ethyl

To a neat mixture of mucic acid (4.2 g, 20 mmol) and propionyl chloride (18 ml, 200 mmol) was added $ZnCl_2$ (0.28 g, 2.0 mmol). The reaction mixture was heated at reflux temperature for three hours. After cooling, diethyl ether (20 ml) was added to the reaction mixture and the solution poured onto ice chips (approximately 100 g) with stirring. Additional diethyl ether (80 ml) was added to the mixture and stirring continued for 30 minutes more. The ether portion was separated, washed with water to a neutral pH, dried over anhydrous $Na_2SO_4$ and evaporated to dryness. The crude product was purified by recrystallization from a cosolvent system of diethyl ether and methylene chloride, collected by vacuum filtration, washed by ice cold methylene chloride and dried at 105° C. (12 hours) to 15 constant weight. The title compound was obtained as a white solid having a $T_m$ of 196° C., 56% yield.

Example 3

FIG. 5, Compound (5), $R_2$=propyl

Mucic acid hexyl ester was prepared as in Example 2, substituting caproyl chloride for propionyl chloride. The title compound was obtained as a white solid having a $T_m$ of 171° C., yield of 68%.

Example 4

FIG. 5, Compound (5), $R_2$=undecyl

Mucic acid lauryl ester was prepared as in Example 2, substituting lauryl chloride for propionyl chloride. The title compound was obtained as a white solid having a $T_m$ of 145° C., yield of 65%.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

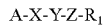

A-X-Y-Z-$R_1$  (I)

wherein A is a carboxy group or is absent; X is a straight chain or branched chain aliphatic group containing 2 carbons to about 20 carbons wherein the aliphatic group is substituted with 2 to about 20 hydroxy groups; Y is —C(=O)—, —C(=S)—, or is absent; Z is O, S or NH; and $R_1$ is a polyether, wherein one or more hydroxy groups of X are acylated with a fatty acid residue.

2. The compound of claim 1 wherein the polyether is linked to X through an ester, thioester, or amide linkage.

3. The compound of claim 1 wherein the fatty acids comprise from about 2 to about 24 carbon atoms.

4. The compound of claim 1 wherein the polyether is a poly(alkylene oxide) having between about 2 and about 150 repeating units, the poly(alkylene oxide) is terminated with hydroxy-, alkoxy-, amino-, carboxy-, or sulfo-group and the polyether is linked to X through an ester or amide linkage.

5. The compound of claim 4 wherein X has from about 3 carbons to about 12 carbons wherein the carbons are substituted with 2 to about 12 hydroxy groups and the poly(alkylene oxide) is terminated with a hydroxy-, amino-, carboxy- or sulfo-group.

6. The compound of claim 4 wherein the fatty acid is lauric, myristic, myristoleic, palmitic, palmitoleic, stearic, oleic, linoleic, arachidic, behenic, lignoceric, eleostearic or erucic acid, or a mixture thereof.

7. The compound of claim 6 wherein the alkylene oxide units contain from 2 to 4 carbon atoms which are straight chained or branched, and X has from about 4 carbons to about 10 carbons wherein the carbons are substituted with 2 to about 10 hydroxy groups.

8. The compound of claim 5 wherein the alkylene oxide is polyethylene glycol with from 50 to 110 repeating units.

9. The compound of claim 1 wherein the polyether is a methoxy terminated polyethylene glycol.

10. The compound of claim 1 wherein X has from about 4 carbons to about 10 carbons wherein the carbons are substituted with 2 to about 10 hydroxy groups.

11. The compound of claim 1 wherein X is substituted with one or more carboxy groups.

12. The compound of claim 1 wherein the polyether is linked to X through an ester or amide linkage.

13. The compound of claim 1 wherein the polyether is linked to X through an ester linkage.

14. The compound of claim 1 wherein the fatty acids comprise from about 6 to about 18 carbon atoms.

15. The compound of claim 1 wherein the fatty acids comprise from about 2 to about 24 carbon atoms and include at least one unsaturated bond.

16. The compound of claim 1 wherein X has from about 3 carbons to about 12 carbons wherein the carbons are substituted with 2 to about 12 hydroxy groups.

17. The compound of claim 1 wherein the polyether comprises alkylene oxide units containing from 2 to 10 carbon atoms which are straight chained or branched.

18. The compound of claim 1 wherein the polyether comprises alkylene oxide units containing from 2 to 4 carbon atoms which are straight chained or branched.

\* \* \* \* \*